United States Patent [19]

Kohr

[11] Patent Number: 5,039,488
[45] Date of Patent: Aug. 13, 1991

[54] DEVICES FOR AMINO ACID SEQUENCE DETERMINATION

[75] Inventor: William J. Kohr, San Mateo, Calif.

[73] Assignee: Genentech, Inc., South San Francisco, Calif.

[21] Appl. No.: 579,202

[22] Filed: Sep. 4, 1990

Related U.S. Application Data

[63] Continuation of Ser. No. 871,736, Jun. 6, 1986, abandoned.

[51] Int. Cl.$^5$ .................. G01N 30/02; G01N 33/68
[52] U.S. Cl. .................. 422/68.1; 210/657; 210/198.2; 422/70; 422/116; 436/89; 436/161; 530/345; 530/408; 530/412; 530/417; 530/810; 530/817; 935/88
[58] Field of Search .................. 422/62, 70, 107, 109, 422/111, 116, 131, 134, 138, 68.1; 436/89, 161; 210/657, 198.2; 435/67, 71.1, 3, 289, 290; 935/88; 530/345, 408, 412, 417, 810, 817

[56] References Cited

U.S. PATENT DOCUMENTS

| | | | |
|---|---|---|---|
| 2,525,497 | 10/1950 | Monfried | 210/290 |
| 3,236,367 | 2/1966 | Patterson | 210/290 |
| 3,615,235 | 10/1971 | Hrdina | 436/89 |
| 3,725,010 | 4/1973 | Penhast | 436/89 |
| 3,787,317 | 1/1974 | Jaworek | 210/502.1 |
| 3,796,657 | 3/1974 | Pretorius et al. | 210/198.2 |
| 3,926,800 | 12/1975 | Stephens | 210/198.2 |
| 4,065,412 | 12/1977 | Dreyer | 436/89 X |
| 4,252,769 | 2/1981 | Hood et al. | 422/50 |
| 4,267,056 | 5/1981 | McClure | 422/70 |
| 4,298,500 | 11/1981 | Abbott | 210/198.2 |
| 4,301,139 | 11/1981 | Feingers et al. | 210/198.2 |
| 4,454,043 | 6/1984 | Ting et al. | 210/659 |
| 4,483,964 | 11/1984 | Urdea et al. | 422/116 |
| 4,517,338 | 5/1985 | Urdea et al. | 422/131 |
| 4,519,905 | 5/1985 | Stevens et al. | 210/198.2 |
| 4,548,904 | 10/1985 | Kent et al. | 436/89 |
| 4,565,632 | 1/1986 | Hatch | 210/198.2 |
| 4,665,037 | 5/1987 | Stolowitz | 436/89 |
| 4,668,476 | 5/1987 | Bridgham et al. | 422/116 |
| 4,679,428 | 1/1987 | Miller et al. | 73/61.1 C |
| 4,746,490 | 5/1988 | Saneii | 422/116 |

FOREIGN PATENT DOCUMENTS

| | | | |
|---|---|---|---|
| 0173233 | 3/1986 | European Pat. Off. | |
| 55-33449 | 3/1980 | Japan | 436/89 |
| 7105603 | 11/1971 | Netherlands | 210/656 |
| 257124 | 11/1969 | U.S.S.R. | 436/89 |
| 8302160 | 6/1983 | World Int. Prop. O. | 422/70 |
| 84/02776 | 7/1984 | World Int. Prop. O. | |

OTHER PUBLICATIONS

Edman et al., European J. Biochem., vol. 1, No. 1, pp. 80–91, 1967.
Hunkapiller et al., Science, vol. 219, pp. 650–659, 2/11/83.
*Protein Sequence Determination*, Ed. by Needleman, Pub. 1975, New York, pp. 232–279.
Wachter et al., FEBS Letters, vol. 35, No. 1, pp. 97–102, 9/1973.
Laursen, Eur. J. Biochem., vol. 20, No. 1, pp. 89–102, 1971.
Lynn et al., Anal. Biochem., vol. 45, pp. 498–509, 1972.
Previero et al., FEBS Letters, vol. 33, No. 1, pp. 135–138, 6/1973.
Strickler et al., Anal. Biochem., vol. 140, pp. 553–566, 1984.
*Methods in Enzymology vol. XXVII Enzyme Structure Part D*, Ed. by Hirs., Pub. by Academic Press, New York, 1973, pp. 942–1011.
Handbook of Spectroscopy vol. 2; p. 543, 1981.
Amino Acid Analysis–Rattenbury 1984, pp. 71–76.
Method of Protein Analysis–1984 Kerusc pp. 159–167.

*Primary Examiner*—Robert J. Hill, Jr.

[57] ABSTRACT

A device for the determination of amino acid sequence of a polypeptide comprises two new features offering great advantages in the cost and efficiency of operation of amino acid sequencers. The sequencer is provided with the capability for the bidirectional flow of sequencing reagents and contains a sample chamber having a bicompositional adsorbent for the polypeptide.

22 Claims, 7 Drawing Sheets

DEVICES FOR AMINO ACID SEQUENCE DETERMINATION

This is a continuation of application Ser. No. 871,736, filed June 6, 1986, now abandoned.

BACKGROUND OF THE INVENTION

This invention relates to methods for the determination of the amino acid sequence of polypeptides and proteins, and equipment for making such determinations.

The most widely used method of protein sequence analysis is the Edman degradation for the sequential removal of amino acid residues. In this scheme, amino acids are removed from the N-terminal of the peptide in a two-step chemical process. The operation for one cleavage is illustrated below.

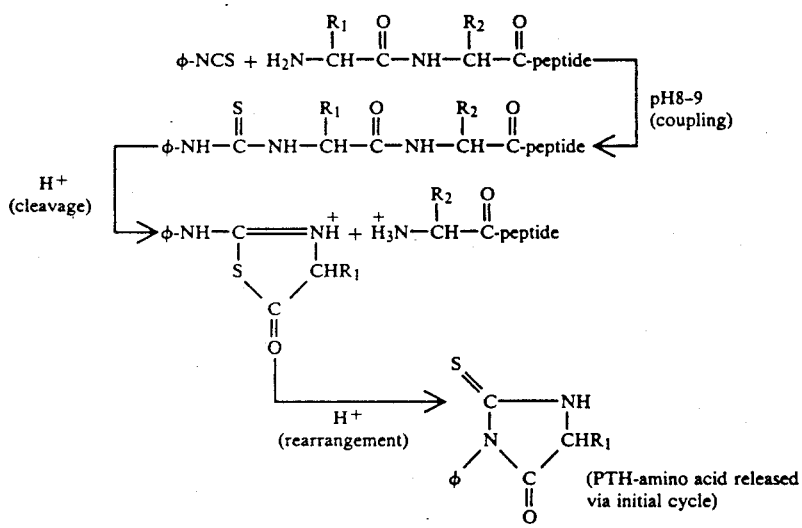

In the first step an activating group, termed a coupling reagent and illustrated by phenylisothiocyanate in the above diagram, is attached to the free amino group of the N-terminal amino acid of the polypeptide, the sequence of which is to be determined. This step is called coupling and is carried out in a buffer containing a coupling base at high pH (pH 8–9). The Edman process typically uses phenylisothiocyanate (PITC) as a coupling reagent. Other reagents such as methylisothiocyanate or penta-fluorophenylisothiocyanate have been used[1,2]. The function of the coupling reaction is to make the peptide bond between the first and second residues more easily acid hydrolyzed than any of the other peptide bonds in the protein. After removal of excess coupling reagent and buffer, the second step is the addition of a cleavage reagent, anhydrous acid, to hydrolyze this activated peptide bond. The cleaved amino acid derivative can then be extracted with a suitable organic solvent. The residual peptide with the newly formed N-terminal is left behind for subsequent cycles. The extracted derivative contains information on the identity of the initial N-terminal residue since the amino acid is incorporated in its structure. By differentiating the twenty or so derivatives on the basis of their side chain ($R_1$), the derivative formed after each cleavage can be identified and the amino acid ascertained. If this process is repeated, each subsequent residue can ideally be determined. However, it is not practical to carry out repetitive chemical reactions indefinitely, since the coupling and cleavage reactions never attain 100% yield Although the coupled N-terminal peptide bond is more susceptible to acid hydrolysis than any other bond, random cleavage can and does occur.

The Edman process has been used in manual methods and in automated methods for amino acid sequence determination.

The manual procedures are most frequently used for sequence determinations of small peptides on short sections of proteins or when the cost of an automated sequencer cannot be justified. Many such methods have been reported[3,5]. Most approaches first apply the protein or peptide to a support such as a paper strip. After the sample is dried, phenylisothiocyanate in a solvent-buffer system (i.e. dioxane or pyridine, etc.) is introduced to the immobilized peptide The coupling reaction may take several hours at 40°–50° C. for completion. It is important at this step that oxygen be excluded to prevent blocking of the N-terminal via side reactions. After coupling is complete, the excess reagents (PITC, etc.) and byproducts (i.e. diphenyl-thiourea) are removed without loss of PTC (phenylthiocarbamyl)-peptides. Several solvent systems have been suggested for this step (.e.g benzene alcohol-ether)[6]. Extraction with benzene alone to remove these byproducts is slow but it does not remove coupled peptides. Either ethyl acetate or an alcohol-ether mixture is better for removing the byproducts but these will also extract small hydrophobic peptides.

After the first wash the PTC-peptide is cleaved into the thiazolinone amino acid and a free peptide. Since internal peptide bond cleavage can occur under aqueous conditions[7], most procedures call for anhydrous acid, such as trifluoroacetic or heptafluorobutyric acid. During this step the reaction is carried out at a lower temperature than when coupling, and water is excluded from the sample chamber. The cleavage of coupled residues is more difficult with prolyl or glycyl residues, and these may require a higher temperature or a longer reaction period. Overly vigorous hydrolysis conditions at this point can lead to spurious cleavage of internal peptide bonds.

In the final step, the 2-anilino-t-thiazolinone amino acid (ATZ) is extracted with benzene and ethyl acetate. The phase transfer is quantitative for most amino acid derivatives except ATZ-Arg and ATZ-His. Ethyl acetate alone will give better extraction of ATA-Arg and ATZ-His but may also extract small hydrophobic peptides. Acetone is a satisfactory compromise if all traces of water and the acid cleavage reagent are removed earlier by drying under vacuum. The extracted ATZ-amino acid is unstable and must be converted to the stable PTH (3-phenyl-2-thiohydantoin) form by aqueous hydrolysis. The method of Edman is generally used. The conversion reaction consists of hydrolysis of the thiazolinone to the PTC-amino acid intermediate followed by rearrangement to the PTH form. The benzene/ethyl acetate extract is evaporated to dryness under a stream of nitrogen and then dissolved in dilute HCL. The temperature is quickly brought to 80° C. and maintained for 10 minutes, then lowered. The solution is dried and dissolved in a small volume of buffer, whereafter the PTH-amino acid derivative is analyzed.

In general, amino acid sequence determinations are made by automated methods in equipment dedicated to that purpose. The chemistry employed in such automated methods is basically the same as that used in the manual procedure. Present automatic sequencers are based on either the liquid phase (spinning cup) or phase designs. In the liquid phase instruments, protein sample is spread out as a thin film on the inner wall of a rotating reaction cup. The protein is immobilized while liquid Edman reagents introduced into the reaction cup at the bottom move up over the protein film by centrifugal force. Liquids are removed from the top of the cup by means of a scoop protruding into a groove around the top of the cup.

A description of the spinning cup sequencer is given in the original paper by Edman and Begg[7]. In the operation of such sequencers a solution of the sample is introduced into the cup and dried under vacuum while the cup is turning, thus forming a thin film on the lower walls of the cup. Sample size is generally around 100 to 300 nanomoles of sample dissolved in about 500 microliters of the appropriate solvent. After the sample has been dried the automatic cycle is started.

The first step is the introduction of coupling reagent (5% PITC in heptane) and buffer into the spinning reaction cup. The buffer generally contains N,N-dimethyl-N-allylamine (DMAA) to maintain the alkaline pH needed for the coupling reaction. A suitable buffer containing DMAA and a detergent is sold under the trademark Quadrol. The coupling mixture spreads out over the Protein film and dissolves it. The ensuing reaction proceeds for about 20 minutes at 55° C. After partial removal of PITC and solvent by vacuum, the coupling reaction is stopped by the introduction of benzene. The benzene precipitates the protein and carries off the excess PITC reagent and some of the breakdown products of PITC. If Quadrol is used as the buffer, the cup is washed with ethylacetate to remove excess buffer and more of the breakdown products. After vacuum drying the protein remains in the cup as a white film Anhydrous heptafluorobutyric acid (HFBA) is added to initiate cleavage. The volatile HFBA covers and dissolves the protein film and after only two to three minutes the N-terminal amino acid is cleaved as the anilinothioazolinone derivative. Finally, the remaining HFBA is removed by vacuum, then the released ATZ-amino acid is extracted with butyl chloride and delivered to a fraction collector. A new residue is released to the fraction collector with each cycle of the above procedure.

The collected fractions of ATZ-amino acids now represent the sequential order of amino acid residues comprising the peptide or protein sample. The fractions can be converted to the more stable PTH-amino acid products The solution is heated for 10 minutes in 1.0M HCl at 80° C. or 25% TFA (trifluoroacetic acid) in $H_2O$ at 60° C. After removal from heat all PTH-amino acid derivatives except PTH-Arg and PTH-His can be extracted with ethyl acetate. Liquid chromatography analysis at this stage is advantageous since there is no need to separate the two phases: All PTH-amino acids present can be determined in a single injection. For preconcentration purposes, the fraction is usually taken to dryness at low temperature prior to the chromatography.

The spinning cup sequencer suffers from the disadvantages of requiring the delivery of precisely calibrated reagent quantities, else protein is easily washed from the cup, the protein must be continuously cycled through successive precipitations and resolubilizations, leading to protein loss and denaturation, and extenders such as Polybrene or blocked proteins are often required to aid in the precipitation of the test sample. The disadvantage of proteinaceous extenders is that they are frequently hydrolyzed during cycles of Edman degradation. These hydrolyzed extenders contain free amino termini that are sequenced along with the test sample, thereby introducing interfering residues into the determination.

Automatic solid-phase sequencers perform the Edman degradation on peptides in much the same way as liquid-phase systems, except that the peptide is immobilized by covalent attachment to a solid support material and does not undergo cycles of solubilization and precipitation Reagents and solvents are undirectionally pumped through a column of bound peptide as required. In this type of sequencer the sample peptide first must be covalently linked to the support material. Several methods have been reported for achieving this task. The most reliable coupling procedures utilize the ϵ-amino group of lysine[10] or a C-terminal homoserine[15]. Coupling yields are usually up to about 80% but the peptide must contain lysine or a C-terminal carboxyl group[16]. The two types of solid supports for covalent coupling generally used are polystyrene[17] and porous glass[13]. Both are highly substituted with functional groups and inert to the reagents and solvents used in sequencing. Small peptides containing lysine are usually attached to aminopolystyrene by the diisothiocyanate coupling procedure. Peptides without lysine are attached to triethylenetetramine resin by carboxyl activation. Large peptides and proteins are affixed to amino glass supports after activation with diisothiocyanate[18].

After peptide attachment the resin is washed and packed into a small glass column. The reaction column is then placed into a heated holder in the sequencer From this point, the solid-phase instrument follows much the same chemical procedure as the manual and spinning cup methods except that a wider range of reagents, buffers and solvents can be passed through the column without fear of washing out the covalently bound peptide. The routinely used solid-phase sequencing chemicals are: PITC (5% V/V in acetonitrile), pyridine: N-methylmorpholiniuatrifluoroacetate buffer (2:3 V/V), and trifluoroacetic acid. Ethylene dichloride and methanol are used as solvents. Fractions of the ATZ-amino acids are collected in a fraction collector and later converted to the PTH-amino acid derivative either manually or automatically as described before.

The solid phase sequencer using covalent immobilization of the test protein has never achieved widespread commercial acceptance. This is predominantly the result of the nature of the covalent immobilization, which requires specialized conditions for each polypeptide and results in protein losses.

The gas phase sequencer is related to the solid phase sequencer in that it uses preimmobilized polypeptide. However, rather than avoiding peptide loss by covalent immobilization, this system uses a gaseous form of the alkaline buffer coupling reagent to avoid elution of non-covalently adsorbed polypeptide. The gas phase sequencer has enjoyed considerable commercial success, supplanting both the spinning cup and solid phase sequencers.

An early version of a gas phase sequencer is described in U.S. Pat. No. 4,065,412. A commercial sequencer based upon the system described in that patent is sold by Applied Biosystems of Foster City, Calif. In that system, the protein or peptide is noncovalently deposited on a glass fiber disc which contains a protein extender (Polybrene). The protein and extender form an immobilized film in the glass fiber disc which is held in a small glass chamber. Gas and liquid Edman reagents enter through a small opening at the top of the chamber and exit through the bottom.

The coupling reagent is added in an organic solvent (heptane) that will not dislodge the peptide. The coupling reaction occurs after wetting of the entire surface of the glass disc with the coupling reagent solution and drying off the organic solvent. The reaction is started by introducing the gaseous coupling base, trimethylamine (TMA) The vapor stream of coupling base and water vapor increases the pH of the protein film. In contrast to the spinning cup sequencer, the sample chamber is small and simple. Since there is no liquid buffering solution, certain peptides may be sequenced without covalent attachment. However, this requires that the coupling reagent be added in an organic solvent and that the coupling base be introduced in a separate step. Furthermore, a disadvantage of using the gaseous coupling base is that the reaction is not as easily controlled as with a liquid buffer solution In solution, the optimum pH is approximately 9.0. At a pH higher than 9.5, the coupling reagent begins to react more rapidly with water to form byproducts (anilide and diphenylthiourea). At higher pH levels, breakdown of the peptide or protein can become a problem as set forth in the aforementioned U S. Pat. No. 4,065.412. To effectively control the pH on the reaction surface, the flow rate of the gaseous phase must be precisely controlled as well as the concentration of base (e.g., TMA) in the gaseous atmosphere. This requirement for precise control of flow rates and concentrations results in a very complex and expensive instrument that requires highly skilled operators. Total instrument temperature control is needed to ensure precisely calibrated reagent aliquots.

Another disadvantage of the gas phase system is the requirement that Polybrene (e g., in amounts of 1.2 mg) be used to retain the protein on the small glass disc. However, Polybrene also retains byproducts more efficiently. It has been reported that covalently linked peptides when sequenced in a gas phase sequencer without using Polybrene produce much less of the byproduct peak[19]. Large amounts of byproduct peaks can obscure the identification of some amino acid derivatives.

Another disadvantage of performing the reaction on the surface of the gas phase sequencer with little if any aqueous solvent is that small amounts of salts, denaturants such as urea, or buffer ions deposited from the test sample can interfere with the reaction of the alpha-amino of the N-terminal residue, or interfere with the solvent extraction of amino acid derivatives for identification or the washing out of undesired byproducts.

Another disadvantage of the gas phase sequencer is that after the coupling reaction is complete, all remaining water vapor must be removed by an inert gas drying. Then the byproducts are removed by flowing an organic solvent through the disc holding chamber. It is important that the flow of solvent be precisely controlled so as not to dissolve or dislodge any immobilized protein. Since the flow is in one direction only and there is no film reforming step in the process, any dissolved peptide is lost in the wash.

It has been conventional for quite a long time to prepare test samples for amino acid sequencing by separating polypeptides from one another or from contaminants through the use of dialysis membranes or high pressure liquid chromatography. However, such procedures have not been incorporated into amino acid sequencing devices, and in fact are considered undesirable because they result in the loss of sample.

Accordingly, it is an object of the invention to provide a sequencer which is less expensive than the sequencers of the prior art in not requiring finely calibrated fluid or gas delivery systems or complete instrument temperature control.

It is a further object of the invention to provide a sequencer which is simpler to use than the systems of the prior art, thereby enabling unskilled persons to operate the sequencer.

It is another object to provide a sequencer capable of a higher percentage repetitive yield than has heretofore been available, and thus which is capable of being employed for a larger number of cycles than prior art systems.

It is another object of the invention to provide a sequencer capable of use with contaminated peptides which have not been previously purified. This avoids protein losses in sample preparation and recovery procedures heretofore used with conventional sequencers. This means that over the combined process of sample preparation and sequencer operation far less polypeptide is required to obtain amino acid sequence.

Another object herein is to provide a system that requires a substantially lower cycle time by optimizing the reaction conditions for and selection of Edman reagents, and which provides for more precise control of the coupling reaction than is possible with commercially available gas phase sequencers.

It is an additional object to provide a system for performing sequencing chemistry in an inexpensive multiple column sequencer for simultaneously determining amino acid sequences on a plurality of test samples, i.e. it is the objective to be able to use inexpensive turret valves with low fluid delivery tolerances in sequencers.

It is still a further object to provide a system for amino acid sequencing wherein the polypeptide is not so denatured or modified as to be insoluble in aqueous reagents. Polypeptides that are allowed to freely associate with water can be more accurately sequenced because the amino terminus is not potentially folded into an insoluble matrix and thus is not inaccessible to the sequencing reagents.

Another object is to dispense with the expense and difficulty of working with protein extenders such as Polybrene.

Another object is to provide a device for amino acid sequencing in which the advantages of temperature control during amino acid sequencing reactions can be fully realized.

An additional object is to provide an amino acid sequencer having replacement sample chamber cassettes for convenience and ease of use.

Further objects and features of the invention will be apparent from the following description taken in conjunction with the accompanying drawings.

SUMMARY OF THE INVENTION

The objects of this invention are achieved by a revolutionary change in the way in which polypeptide test samples are handled in amino acid sequencing systems. Whereas heretofore the art has considered it to be essential that the test sample be rigidly immobilized during at least part of the treatment with liquid Edman reagents in order to prevent protein losses due to wash-out from the sample chamber, applicant has recognized that many advantages are achieved if the test sample is in fact free to migrate within the sequencer sample chamber and should not be immobilized or precipitated therein. Applicant has avoided sample wash-out that otherwise would attend non-immobilized polypeptide by two major changes in prior art liquid phase sequencers. First, the improved sequencer is capable of multidirectional flow through the sample chamber. This permits reagents to be introduced serially at opposed ports in the sample chamber whereby the test sample migrates first in one direction with one solvent and then in the opposite direction by another solvent.

Second, in a preferred embodiment the sample chamber also contains a plurality of discrete adsorbents for the polypeptide tandemly arrayed in the solvent flow path through the chamber. The adsorbents are chosen so that the polypeptide sample partitions between a first adsorbent and solvent differently than between a second adsorbent and the same solvent. This means that a given polypeptide will migrate more slowly through the chamber (and its tandem adsorbents) in one direction than in another when the chamber is eluted with a given solvent. This is combined with the multi-directional flow embodiment described above to focus water soluble polypeptide in a band within the chamber that is poised between the chamber ports, i e. it migrates to and fro within the chamber as sequencing reagents are introduced but, because of the use of multiple adsorbents of opposed characteristics and multidirectional flow, the sample is not washed out of the sample chamber.

According to a preferred embodiment of the present invention I provide a polypeptide sequencer comprising (a) a flow-through sample chamber defining a fluid flow path and having first and second ports along the flow path, (b) chromatographic medium disposed in said sample chamber along the flow path, and (c) means for the sequential introduction of fluid reagents alternately to said first and second ports, whereby fluid reagents may be passed sequentially in opposite directions along said chromatographic medium flow path.

In the preferred embodiment, the sample chamber contains a tandem array of distinct adsorbents having differing solid phase. solvent partitioning properties with respect to the sample polypeptide. This is used together with multidirectional flow to suspend the polypeptide within the sample chamber.

A preferable chromatographic medium includes two discrete chromatographic medium segments in tandem of differing chromatographic properties, most preferably one hydrophilic and the other hydrophobic.

A convenient feature of the sequencer of this invention is that the sequencing reactions are performed in a container having first and second ports and disposed therein within the fluid flow path a plurality of discontinuous adsorbents, preferably chromatography resins, in tandem array in the fluid flow path.

In an exemplary method, water soluble peptide is deposited onto the chromatographic medium and migrated to the interface between the segments. The sample then is contacted with coupling reagent and coupling base flowing in a first direction to conjugate the coupling reagent to the peptide. Then a liquid washing solvent is flowed in the substantially opposite direction to remove unreacted coupling reagents and contaminants. Thereafter, cleavage reagent flows through the reaction in the first direction to cleave amino acid derivatives from the coupled peptides. Then, a liquid extracting solvent is flowed through the sample chamber in the second direction to extract and withdraw the cleaved amino acid while leaving the remaining peptide poised in the chromatographic medium. In all of the foregoing liquid elutions the direction of the flow is chosen so that the polypeptide migrates from a "fast" resin into a "slow" resin for the solvent concerned. A "fast" resin is one in which the polypeptide partitions to a greater extent into the solvent phase and therefore migrates through the resin more quickly than through the "slow" resin, which has a higher affinity for the polypeptide in the same solvent The amino acid derivative is then withdrawn and analyzed and the procedure is repeated for successive amino acid derivatives. The flow reversal permits migratory chromatofocusing of the peptide in the sample chamber.

DETAILED DESCRIPTION OF THE PREFERRED EMBODIMENTS

The present invention is directed generally to sequencing proteins or peptides by repeated cycles of attaching coupling reagent to a terminal amino acid and cleaving the coupled amino acid derivatives. For simplicity of description, the term peptide will include both peptides and proteins as sample materials. The invention is particularly adapted to the basic Edman procedure set forth in the background. The present application will refer to that procedure. However, it should be understood that by appropriate modification, the method is also applicable to other sequencing procedure which includes the same functional steps.

Figure 1:
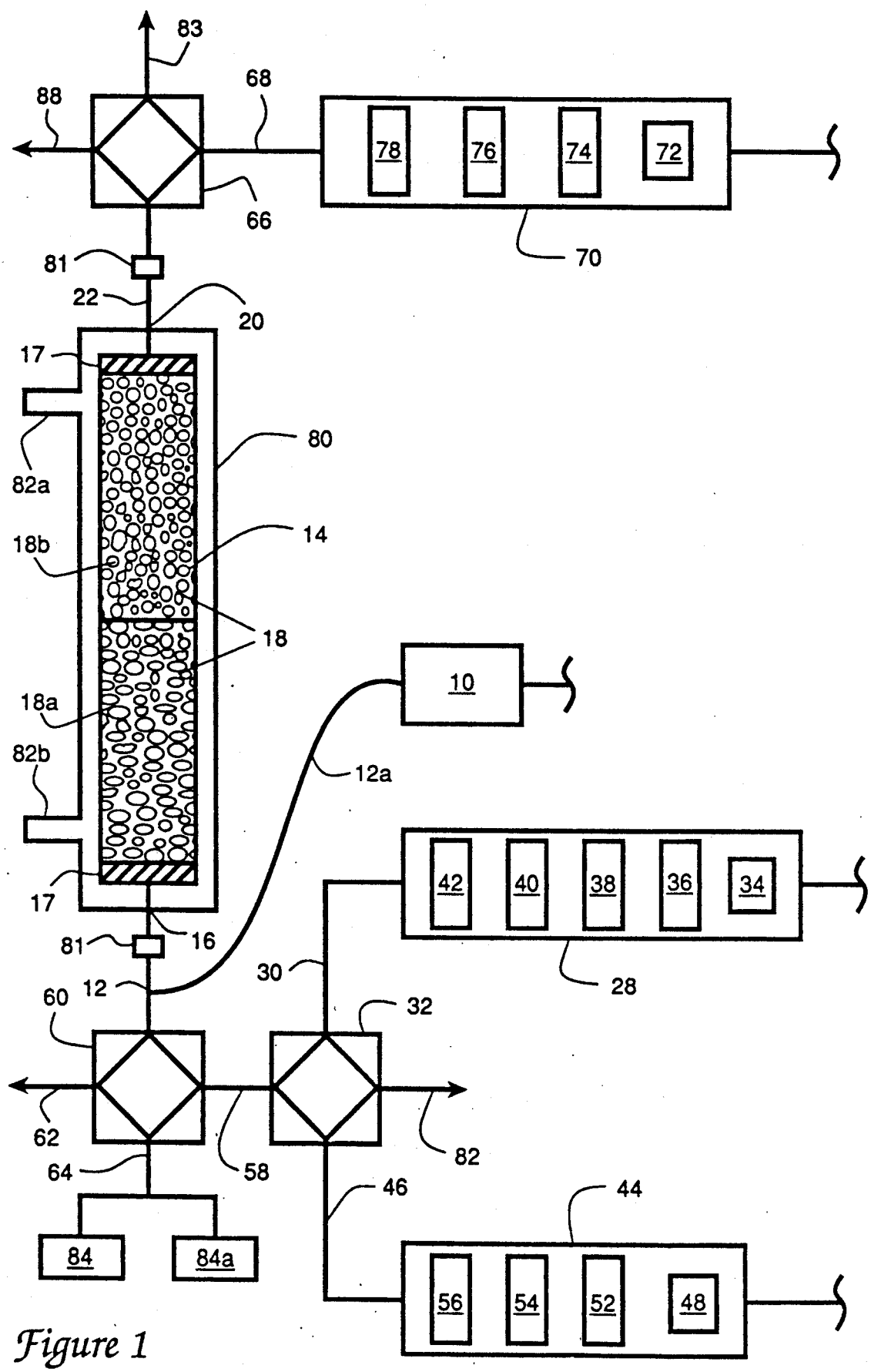
FIG. 1 is a schematic representation of a bidirectional flow, biphasic resin sequencer for use in the present invention.

Referring to FIG. 1 a sequencer suitable for use in the present invention is illustrated. Aqueous sample solution containing peptide is injected through injection valve 10, such as is supplied suitably by a syringe. Sample solution through line 12a to line 12 which loads flow-through sample chamber 14 manually or automatically via flow-through port 16 disposed at one end of chamber 14. Chamber 14 preferably is in the form of an elongate flow-through column which is transparent to light (e.g., formed of glass). The total volume of the chamber can be varied but is generally about 0.20 ml including about 20 to 40 mg of dry glass beads. Chamber 14 contains chromatographic medium 18 having at least distinct first chromatographic medium segment 18a and second chromatographic medium segment 18b of differing chromatographic properties in fluid communication with each other along the flow path of the column. Segments 18a and 18b preferably are in tandem and abut each other to form an interface. Medium 18a is preferably hydrophilic, while medium 18b is preferably hydrophobic. Other suitable chromatographic media include Synchhropak AX300, Q300, CM300, or S300, which are amion and cation exchange HPLC supports.

In the illustrated embodiment, the lower stationary phase, chromatographic medium 18a is hydrophilic in the form of a normal phase HPLC medium. It should have a long retention time for the hydrophilic group of the peptide and a low affinity for the hydrophobic side products of the Edman reaction. Controlled-pore glass (e.g., supplied by Electro-Nucleonics, Inc., Fairfield, N.J.) or Silica, termed Nu-Gel, may be used as this lower stationary phase. A suitable volume of this segment 18a is 0.1 ml. The characteristics are as follows: Nu-Gel 952 AC 200 angstrom pore size, 200–400 mesh.

The hydrophobic upper phase segment 18b is formed of reverse phase HPLC material such as alkyl (C8 to C18) coupled silica. This material has good flow characteristics and is resistant to reagents used in sequencing. A suitable volume of this segment 18b is 0.1 ml. The characteristics of Synchroprep coupled silica are as follows: 300 angstrom pore size, 30 micron particle size.

While the double stationary phase system is preferable because of its ability to retain the peptides as described below, it should be understood that a single phase, preferably of the hydrophilic type may also be employed with bidirectional flow.

Overall, the importance of the chromatographic phase is that the peptide which is mobile, i.e., not covalently bonded to the chromatographic material but rather reversibly adsorbed, is retained by this system when passing upwardly in an aqueous solution because of the use of the reverse phase material. The normal phase lower column retains the peptide when conducting organic solvent downward for extraction of excess reagent, byproducts and the amino acid (ATZ) derivative.

The chromatographic medium is preferably a particulate bed retained in place during liquid flow by a suitable material at its top and bottom ends which permits passage of fluid but not of the particulate chromatographic bed. As illustrated, such retention means comprise porous plugs 17 suitably formed of glass or Teflon wool.

Referring again to FIG. 1, line 12 is removably sealed to port 16. Chamber 14 is provided with a second port 20 at its upper end which communicates with line 22. The system is fluid tight at ports 16 and 20. Appropriate releasable fittings or couplings (81) are provided at both ends for ready engagement and disengagement with the sequencer to form a fluid-tight seal at ports 16 and 20 in a conventional manner. In this way, after completion of the sequence, chamber 14 becomes a cartridge which may be removed from the sequencer and preferably replaced with a clean cartridge for each run to avoid cross contamination of peptides.

Figure 3:
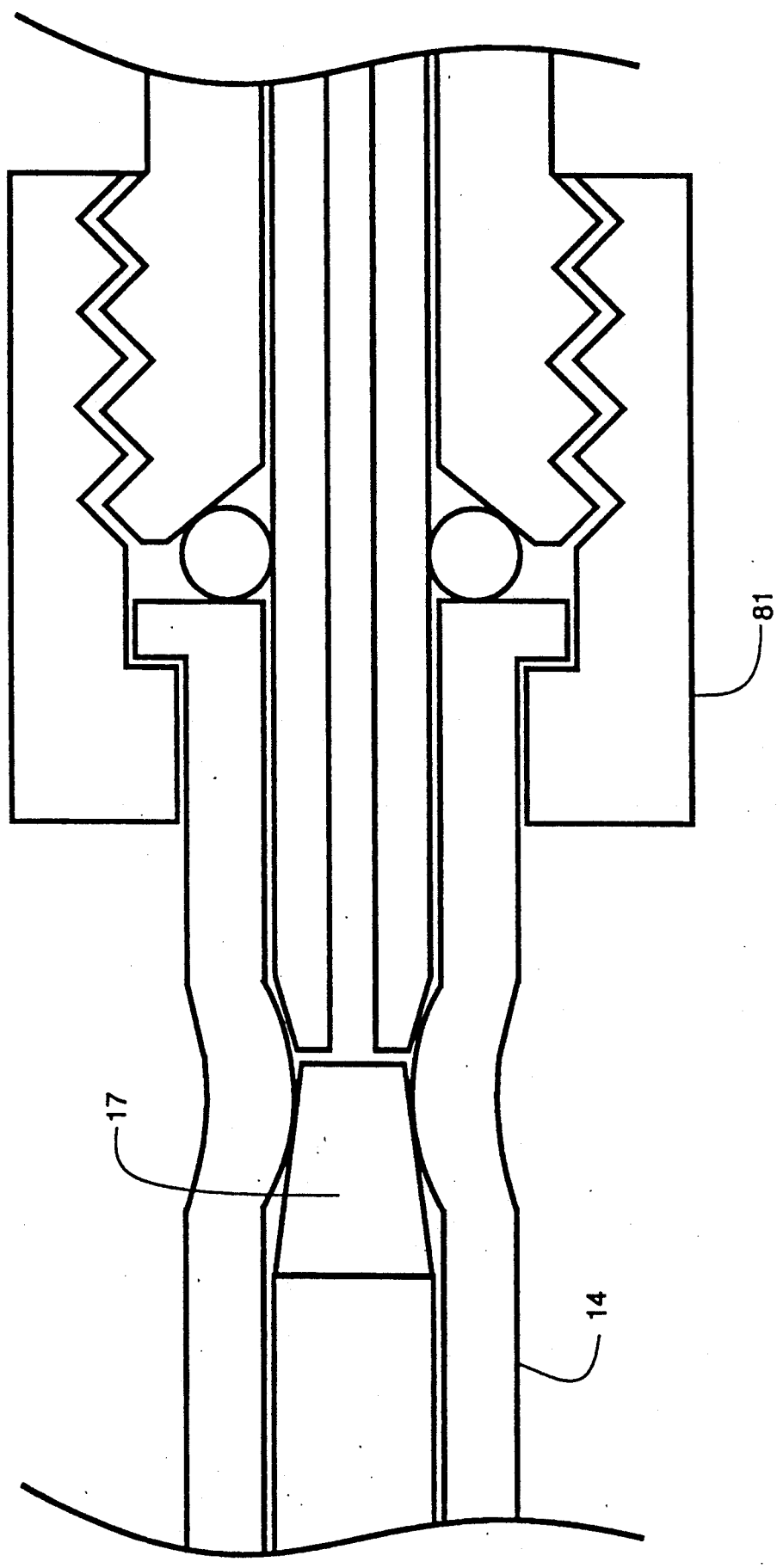
FIG. 3 illustrates a cut-away view of the symmetrical end of preferred cassette or cartridge sample chamber for use in the sequencer herein.

A suitable sample chamber is a small glass column, (2mm in diameter) which may be equipped with suitable means for temperature control such as a water jacket 80 through which temperature adjusted fluid is passed via conduits 82. The column fitting at the lower end 81 may be formed by melting the column to restriction into which a piece of small bore [1.5 mm] Teflon tubing is wedged to a tight fit (see FIG. 3). The tubing may then be held tight by spring tension or an O-ring and screw fitting.

The system includes first reservoir means or block (including reagent, coupling reagent and coupling base containers), generally designated by the number 28. Flow from block 28 proceeds through line 30 to four way valve 32. As illustrated, block 28 includes a source 34 of pressurized inert gas (e g., nitrogen), a solvent container 36, a vapor buffer (coupling base) container 38, a liquid buffer (coupling base) container 40 and coupling reagent (PITC) container 42. The terms "buffer" and "coupling base" are used interchangeably.

The system also includes a cleavage reagent block 44 connected by line 46 to valve 32. Block 44 includes a source 48 of inert gas, a solvent container 52, a container 54 of cleavage reagent (TFA) vapor and a container 56 of liquid cleavage reagent (TFA). Valve 32 is connected by line 58 to a second four-way valve 60 including one position to waste line 62 and another position for passing derivatized amino acid into line 64 communicating with a suitable detector 84. Line 12 interconnects sample chamber 14 and valve 60.

Line 22 is connected to four-way valve 66 which is in turn connected by lines 68 to a series of containers in a solvent block, designated by the number 70. Block 70 includes in sequence a source 72 of inert gas, valved container 74 for acetonitrile solvent, valved container 76 for ethyl acetate solvent, and valved container 78 for benzene solvent. A high pressure valve (not shown) may be interposed in line 68 between the solvent reservoirs and the valve 66.

For convenience of description, the sample chamber will be described in a vertical orientation with port 16 designated the bottom and port 20 designated the top. However, it should be understood that orientation of the sample chamber does not affect the procedure. For example, it may be inverted or disposed horizontally. In the present description, the bottom will refer to the inlet adjacent to the normal or hydrophilic chromatographic medium (the "lower medium") while the top designation will refer to the port adjacent to the reverse phase or hydrophobic chromatographic medium (the "upper medium").

Methodology

Figure 2A:
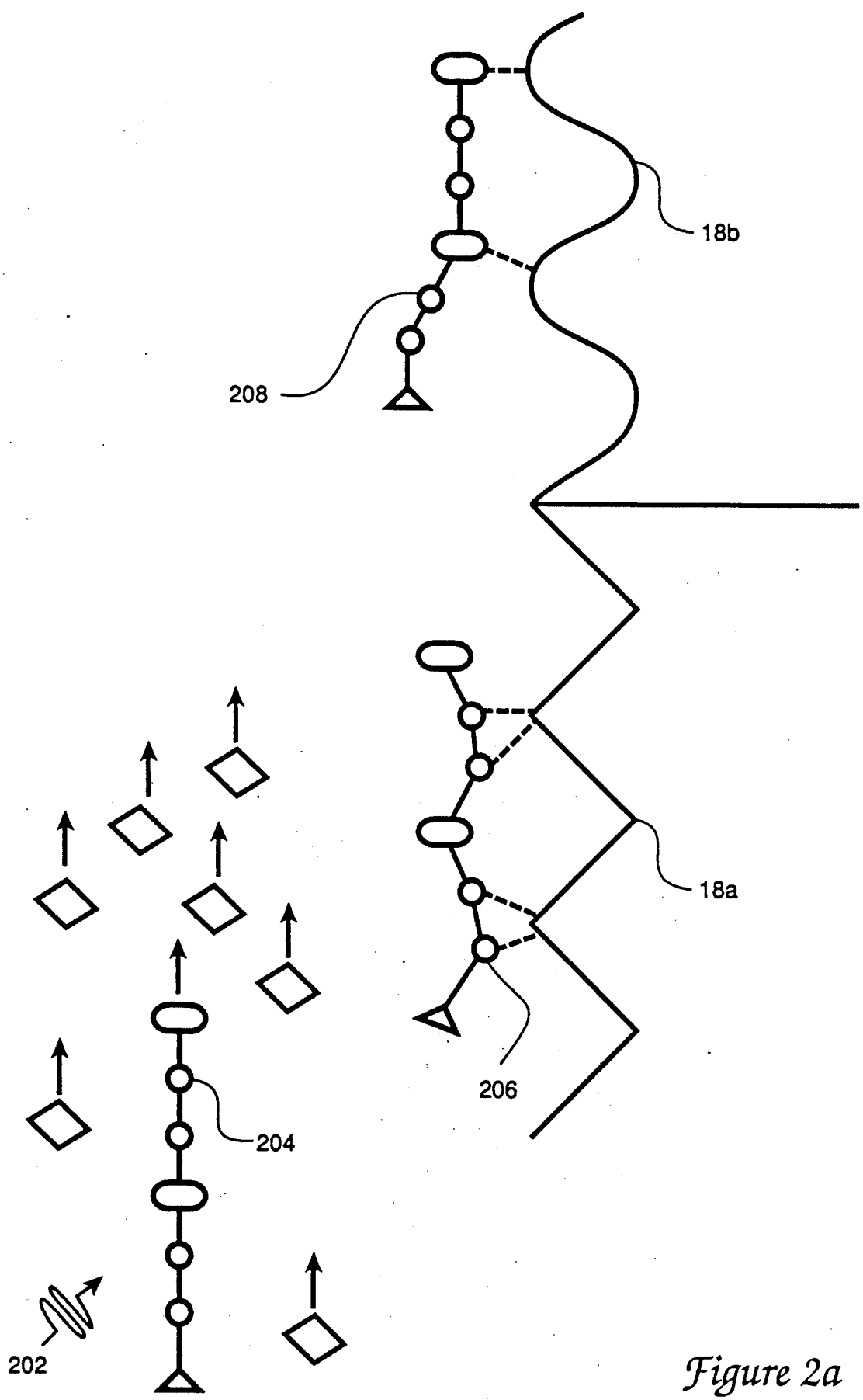
FIGS. 2a–2e illustrate the steps performed in using the inventive device herein with the Edman sequencing method.

In step 1 (FIG. 2a), a sample 202 in injection valve 10, suitably in an aqueous solution, is loaded from the bottom of the column by injecting sample 202, including 204, 206 and 208 through line 12a and line 12 into chamber 14. Most proteins and some peptides 206 will be retained by the hydrophilic lower medium segment 18a. Proteins and hydrophobic peptides 208 can be supplied in solutions with high concentration of salts and other denaturants (e.g., urea, SDS, sucrose and the like). If the protein is in a high concentration of salt or denaturant, it may elute from lower medium segment 18a and migrate up into segment 18b, where it is retained as illustrated by released protein 208 in FIG. 2a. The solution that passes through the column may be collected for analysis to verify that all of the protein is retained by the column. In this instance, valve 60 is in a bypass position while valve 66 is in the illustrated position with excess solution being collected at line 88. Solvents from block 70 are vented to waste through line 83.

Typically, medium 18 is flooded with aqueous sample solution so that the protein in the solution migrates upwardly through the column but is retarded by the hydrophobic upper medium segment 18b. It is noted that although it is preferable to load the peptide from the bottom of the system, it may also be loaded from the top.

Step 2

In this step, wash solution injected at injection valve 10, previously used for the sample, flows upwardly through the column and line 80 for removal to a wash collection vessel. The wash solution may be water or a low concentration of acetonitrile as a mobile phase which preferably flows from the bottom to the top of the column and out the top. In this step, the remaining salts denaturants or small unwanted peptides or amino acids are removed from the sample chamber. Steps 1 and/or 2 may be performed automatically or manually and chamber 14 may be disconnected and stored for subsequent sequencing. In an alternative embodiment the aqueous sample and wash solutions may be introduced into chamber 14 while chamber 14 is disconnected from the sequencer, with subsequent attachment to the sequencer.

Step 3

In this step, suitable coupling reagent (PITC) is delivered in a suitable solvent (e.g., acetonitrile or heptane), preferably 2% PITC in heptane and the reactants are maintained at about 55° C. in the column. See FIG. 2b. In one embodiment, the a coupling base [buffer] 40a 42 first is directed through valves 32 and 60, then through line 62 to waste, thereby filling the dead volume between the two valves (58). Thereafter, the positions of valves 32 and 60 are changed simultaneously and inert gas in source 48 of block 44 is directed to pass the precisely controlled amount of coupling reagent in the dead volume loop 58 between valves 32 and 60 into the bottom of reaction column 14. This embodiment using carefully controlled volume is optional but preferred. Once the coupling reagent is passing into the column, the unused portion of the reagent in valve 32 may be washed out by passing inert gas from source 34 through line 30 and valve 32 to waste as designated by line 82.

In an alternative mode, step 3 may be performed by delivering the coupling reagent from container 42 directly through valves 32 and 60 to the bottom of the reaction column simply by opening the coupling reagent 12a control valve (not shown) with valves 32 and 60 connected to the reaction column. This technique is less preferred because the volume of coupling reagent which passes through the sample chamber is not controlled as precisely as the above referred mode using a precise loop volume. This mode can be used in the usual case where the peptide is retained by the hydrophobic segment 18b. In this alternative mode, it is preferable to carry the PITC in heptane rather than acetonitrile to avoid elution of small peptides from the top of the hydrophilic medium section if a large amount of coupling reagent were inadvertently used.

After either of the above two procedures of delivering coupling reagent, it is preferable to dry the system by flow of inert gas either from the top or bottom of the sample chamber from sources 34, 48 or 72. This drying serves the function of removing the solvent. However, it is an optional step.

Step 4

In this step, a coupling base (buffer) 40a (FIG. 2b) is delivered in an analogous manner to that of step 3.

The loop method described first above can be used to deliver a small precisely controlled amount of liquid buffer to protect against successive amounts being delivered which may carry small peptides up the column. The liquid buffer may be combined with volatile buffer (e.g., trimethylamine or triethylamine and water) from source 28. Since the amount of liquid delivered in this manner will typically be too small to entirely wet the chromatographic medium, the peptide will migrate upwardly through the column but not out of the sample chamber. If the peptide is so large as to be retained on the hydrophobic medium, an amount of liquid buffer 40a may be used that exceeds the column volume. This takes advantage of the two phase discontinuous hydrophilic-hydrophobic system to focus the large peptide at the interface between the normal phase support and the upper reverse phase support.

The volume of liquid buffer delivered is increased beyond the column volume by first opening the liquid buffer valve for container 40 in block 28 so that the liquid flows through valves 32 and 60 and to waste via line 62. Then, valve 60 is shifted in position to direct the liquid buffer upwardly through line 12 to the column shortly (e.g.. two seconds) before valve 32 diverts flow to waste via line 82. Inert gas from source 48 in block 44 is used to force the buffer through valve 60 and line 12 into the bottom of the reaction column 14. This timing can be adjusted so that sufficient liquid buffer enters the sample chamber to wet the entire chromatographic medium 18 with excess buffer free to be eluted through the top of the column. The following criteria are used to select the coupling base. The coupling base will control the pH to within the range from 8-10 and will dissolve both peptide and coupling reagent Suitable coupling bases include hydrophilic solutions such as Quadrol, DMAA, DMBA, or the like, but preferably supplied with a propanol content lower than that present in conventional sources of these products (e.g., 5-20% or less). Such a hydrophilic solution typically causes moderate migration of the peptides upwardly through the hydrophilic chromatographic medium but very slow migration at best through the hydrophilic medium segment.

The flexibility of this system to permit use of such high volumes of liquid buffer 40a permits an increase in efficiency of the coupling reaction by precise pH control. If desired, the liquid buffer can also contain detergents such as SDS to help solubilize the protein. Another reagent that may be included is Norleucine, a primary amine similar to natural amino acids, which may be used as an internal standard and carrier-scavenger for PTC amino acid.

Figure 2B:
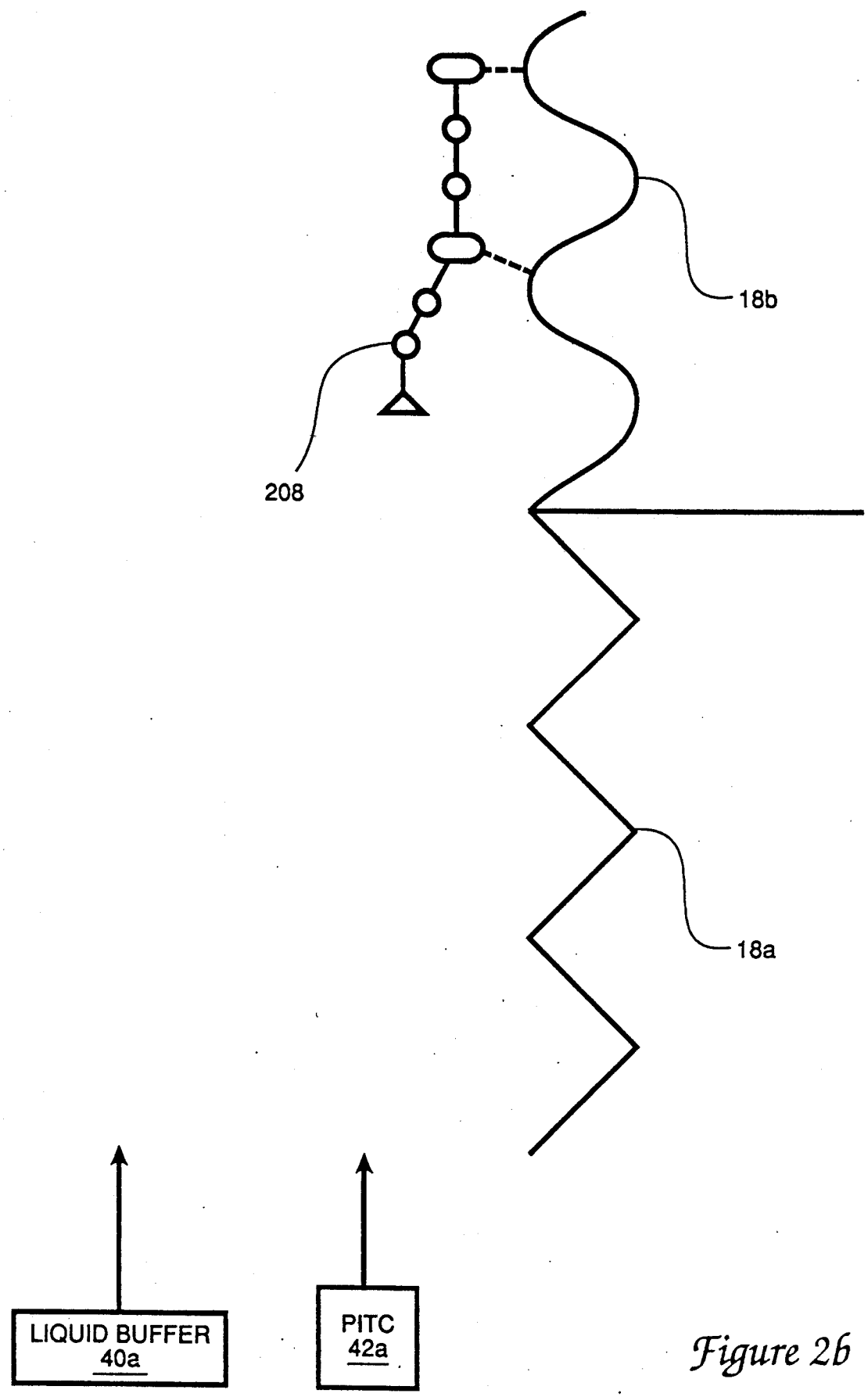

Although Steps 3 and 4 are described in terms of sequential addition of coupling reagent and coupling base, it is only important to the reaction that the two reagents be in simultaneous contact with the peptide as shown in FIG. 2b. Thus, the system can be operated by combining steps 3 and 4 with the combined addition of coupling reagent and coupling base.

Step 5

In this step, the column is dried by flow of inert gas after completion of the coupling reaction. In a preferred technique, the gas first is directed upwardly so that aqueous liquid flows in the direction of hydrophobic material. This may be accomplished by passing inert gas from source 34 through valves 32 and 60 and line 12 upwardly through the column. Then, after most of the liquid is removed, the drying may be completed by high pressure gas such as supplied by inert gas source 72 through a high pressure valve in line. 68. The gas then flows through valve 66 and line 22, column 14 line 12, valve 60, line 62 and out to waste. Complete removal of water is desirable but is not as critical as in prior techniques such as a spinning cup sequencer or gas sequencer described above. This is because migration of the peptide due to the water which causes the organic mobile phase to become more hydrophilic would be counterbalanced by the next addition of liquid buffer from the bottom which causes refocusing of the peptide back towards the interface between the hydrophilic and hydrophobic material.

During downward movement of the high pressure gas, valve 32 may be washed by the passage of solvent from container 36 through the valve and to waste along line 82.

Step 6

In this step (FIG. 2c), organic solvents 70a are passed through the sample chamber in a downward direction to remove non-volatile side products and remaining buffers from the column. The solvents used for elution range from very non-polar solvents such as heptane and benzene to solvents of more moderate polarity such as ethyl acetate or acetonitrile. All solvents enter from the top of the column and are eluted down and out of the bottom of the column. Typically, the solvents delivered in line 68 through valve 66 and line 22 have a pressure on the order of about 10 psi to 100 psi. Valves in the containers in block 70 must be able to withstand pressure of up to 100 psi from source 72 so that high pressure inert gas is flowed through the column to compress any gas bubbles that may trap remaining side products or reagents.

Step 7

Figure 2C:
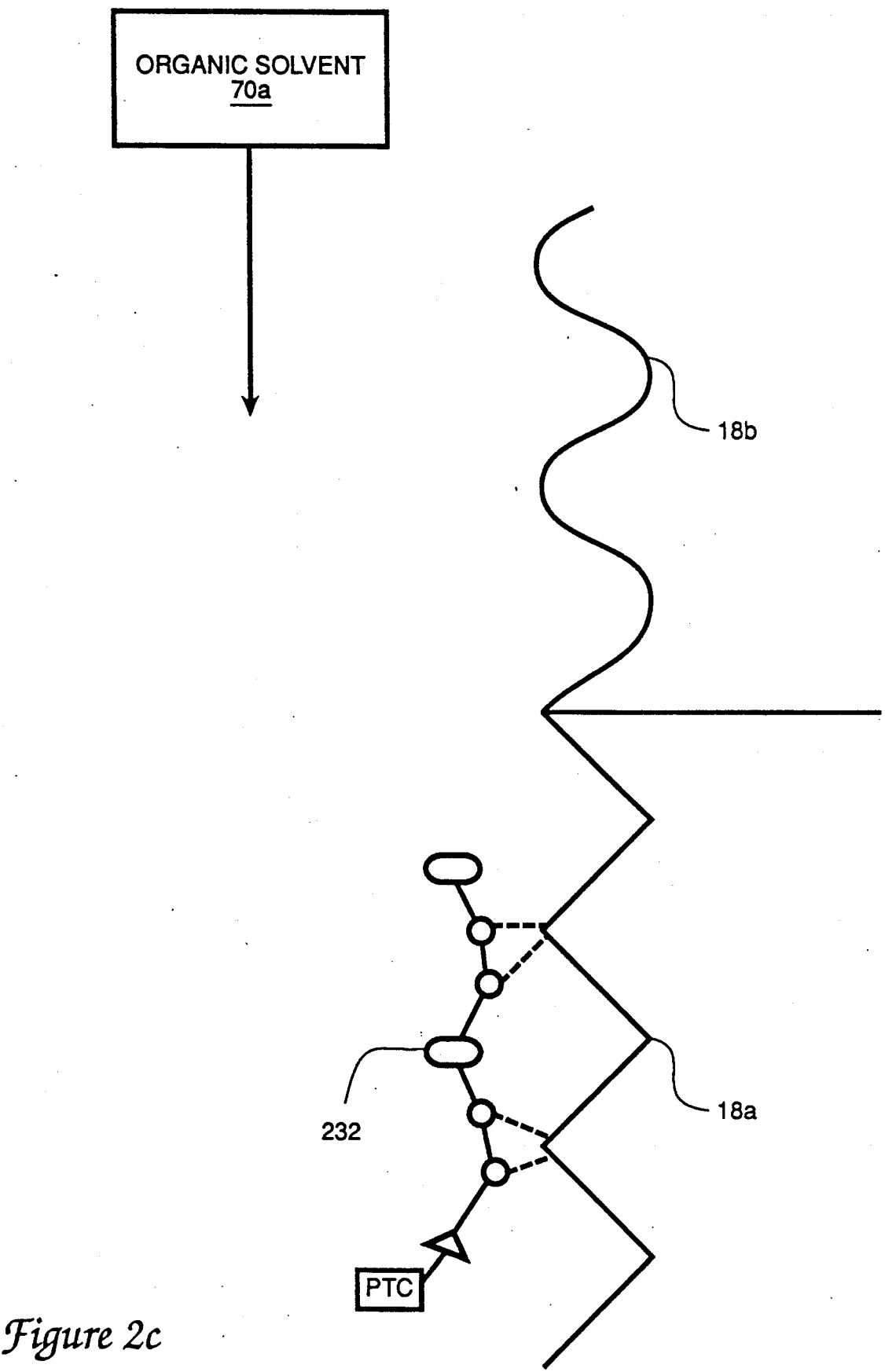
Figure 2D:
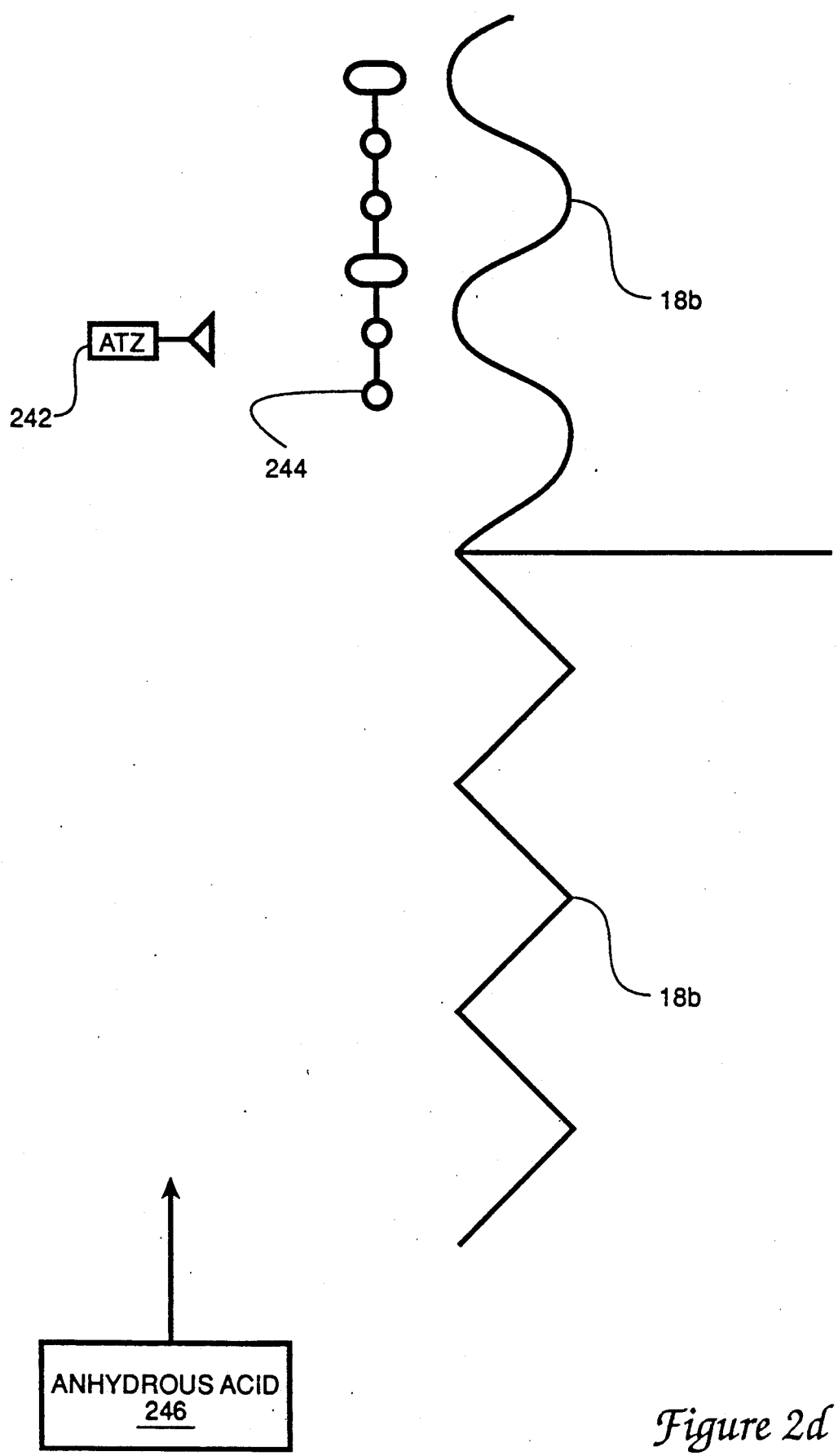

In this step, a coupled (PTC) peptide 232, as shown in FIG. 2c is cleaved with a cleavage acid (FIG. 2d). The temperature for acid extraction is about 0° C. to 50° C. The following criterion is used to select the appropriate cleavage acid 246: It must be anhydrous and volatile and of low enough pH to cause cleavage of the PTC peptide into the thiazolinone (ATZ) amino acid 242 and a free peptide 244 of one less amino acid. Cleavage may be performed with either a liquid acid (HFBA, TFA, PFPA, or the like in an anhydrous solution of acetic acid or acetonitrile, or the like), an acid vapor or a combination of both. The liquid acid increases the kinetics of the reaction. On the other hand, use of the gas reduces the risk of elution of the peptide off the top of the column. Thus, the liquid acid is preferred for shortened reaction times where the peptide is relatively large and so the risk of elution from the column is not great. The system may operate with liquid acid at the beginning stages of sequencing and with a gas phase acid at the later stages when the peptide chain is reduced substantially.

Referring to the use of acid vapor cleavage, vapor from container 54 is directed through line 46 and valves 32 and 60 through line 12 into the bottom of sample chamber 14. The same flow system is used for delivery of the liquid cleavage acid from source 56.

It is preferable to perform the cleavage reaction at a temperature of 10° C. to 50° C. The temperature may be varied by the temperature of the circulating water in the water jacket 80. The reaction is stopped by drying of excess liquid or gaseous acid by an upward flow of inert gas followed by high pressure downward flow as described above Drying may be more complete than in either the gas phase sequencer or spinning cup sequencer. This is because the extraction of the cleaved ATZ amino acid may be performed with a more polar solvent than in these two systems because of the chromatographic separation of ATZ amino acid from the remaining peptide. The extraction does not depend on a small amount of remaining acid as in these prior art techniques.

Step 8

Figure 2E:
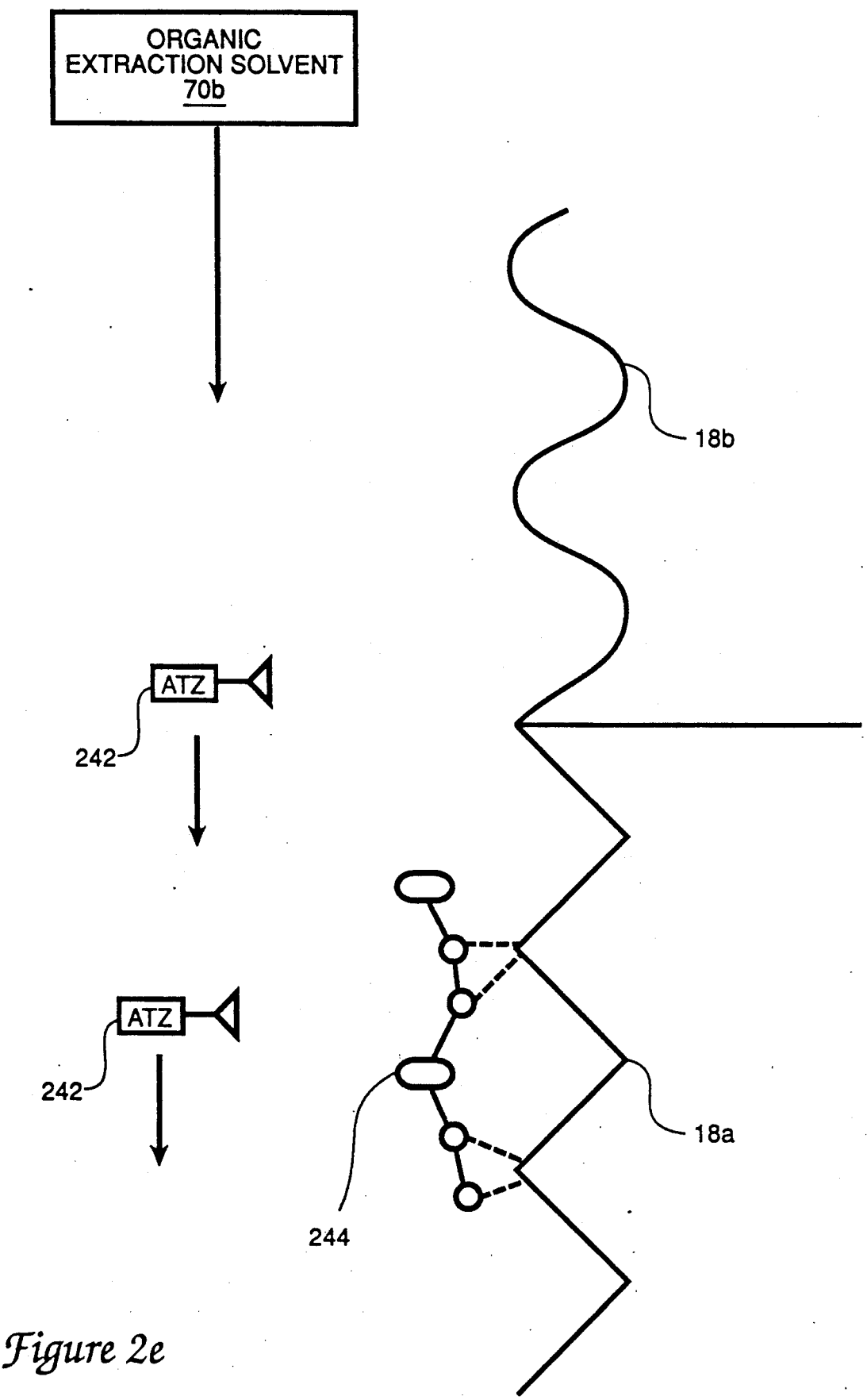

In this final stage (FIG. 2e), the cleaved ATZ amino acid 242 is extracted with a suitable organic extraction solvent 70b such as ethylacetate or acetonitrile. Criteria for selecting the solvent are as follows: Complete elution of all ATZ amino acids but some migration of free peptide through the resin.

As illustrated, solvent 70b from container 76 is passed through valve 66 and through line 22 downwardly through the column through valve 60 and line 64 and to a suitable reaction vial 84a for subsequent reaction. The cleaved ATZ amino acid 242 in solvent is converted in such a vial, not shown, to stable PTH amino acids in a conventional manner. As is typical, the vial can contain or have added to it an aqueous solution of TFA for the aqueous acid conversion. An inert gas is flowed through the sample chamber in a manner described above to remove remaining organic acid. Then the column is ready for the sequencing procedure to be repeated for subsequent ATZ amino acid derivatives.

After conversion of the ATZ-amino acids 242 to PTH-amino acids by reaction with the acid (not shown), the residues can be identified by suitable liquid phase chromatography.

One advantage of the above system is that the sample chamber can be bypassed so that the reagent delivery system can be washed directly to waste. Furthermore, in the case of a microsequencer, the volume of the valve and lines needed to deliver all reagents used in Edman degradation chemistry can be as large as the column volume. Bypassing the sample chamber eliminates the problem of washing excess reagents remaining in the valves and lines to waste via the sample-containing sample chamber. This reduces the amount of solvent flowing over the sample. Excess washing by solvent is detrimental due to extractive losses of sample as well as oxidation of the PTC-peptide by trace amounts of peroxide in solvent. The valve in-line washing process can proceed while the sample chamber is being dried which helps reduce the time of the wash.

A major advantage of this system is the ability to use a mobile phase of the peptide without covalent attachment to the medium but without washout of the sample. The liquid reagents are chosen to dissolve the peptide to cause migration in the direction of flow. By alternating flow directions, the peptide moves up and down the column and tends to focus at the interface between the hydrophilic and hydrophobic phase. The rate of migration will depend upon the partitioning between the mobile phase (liquid reagent) and stationary phase (chromatographic medium).

To illustrate focusing of the peptide in the column, a sample of peptide in an aqueous solution loaded into the sample chamber, flows upwardly through the column. Some peptide typically is contained in the hydrophilic lower segment while other peptides are retained by the hydrophobic upper segment. Low molecular weight components are eluted off the column. During the coupling step the aqueous coupling base and the coupling reagent pass upwardly trough the column and the peptide tends to move upwardly into the hydrophobic medium. Thereafter, in step 6, the organic solvents pass downwardly through the column to again move the PTC amino acid towards the hydrophilic phase. Then, in step 7, the cleavage acid again passes upwardly into the column to move the peptide towards the hydrophobic section. Finally, the extraction of the ATZ amino acid derivative is performed in a downward direction. This bidirectional movement of the peptide by varying the direction of flow between the hydrophilic and hydrophobic chromatographic sections causes a focusing of the peptide near the interface between the two segments to prevent washout of the peptide during the procedure.

The references grouped in the following bibliography and respectively cited parenthetically by number in the foregoing text, are hereby incorporated by reference.

Bibliography

1. S. Datta, et al., Biochem. and Biophys. Res. Commun., 72 (1976) 1296-1303.
2. R.A. Laursen, J. Am. Chem Soc., 88 (1966) 5344-5346.
3. P. Edman. "Protein Sequence Determinations," S.B. Needleman, ed., Springer-Verlage, New York (1975) 237.
4. H.D. Niall, "Automated Edman Degradation: The Protein Sequencer," Methods Enzymol., XXVII (D) (1974) 942.
5. G. E. Tarr, Anal. bIOCHEM., 63 (1975) 361-370.
6. H. Fraenkel.Conrat, J. Am. Chem. Soc., 76 (1954) 3606.
7. P. Edman. et al. Eur. J. Biochem., 1 (1967) 80-91.
8. H. Fraenkel-Conrat, et al. "Recent Developments in Techniques for Terminal and Sequence Studies in Peptides and Proteins," Methods of Biochem: Anal., Vol. 2, D. Glick, ed., Interscience, New York (1955) 359-425.
9. M.A. Hermodson, et al. Biochemistry, 11 (1972) 4493-4502.
10. R. A. Laursen, et al. FEBS Lett., 21 (1972) 67-70.
11. J D. Lynn, et al Anal. Biochem., 45 (1972) 498-509.
12. K. Titani, et al. Nature (New Biol.), 238 (1972) 35-37.
13. E. Wachter, et al. FEBS Lett., 35 (1973) 97-102.
14. M.D. Waterfield, et al. Anal. Biochem. 38 (1970) 475-492.
15. M.J. Horn, et al. FEBS Lett. 36 (1973) 285-288.
16. A. Previero, et al. FEBS Lett , 33 (1973) 135-138.
17. R.A. Laursen, Eur. J. Biochem., 20 (1971) 89-102.
18. R.A. Laursen, "Solid Phase Methods in Protein Sequence Analysis," Pierce Chemical Company, 1975.
19. J.E. Strickler, et al. Anal. Biochem., 140 (1984) 553-566.

I claim:

1. An amino acid sequencer comprising:
   (a) a sample chamber defining a fluid flow path and having first and second ports along said flow path;
   (b) a plurality of discontinuous, tandemly arrayed first and second chromatography resins for adsorption of polypeptide, said first chromatography resin including a hydrophilic resin and said second chromatography resin including a hydrophobic resin, said first and second resins being in contact with one another without substantial intermixing and disposed in said chamber in fluid communication with one another along said flow path; and
   (c) positive pressure means for the sequential introduction of fluid reagents into said chamber alternately through said first and second ports.

2. The sequencer of claim 1 wherein said first and second chromatography resins are high pressure liquid chromatography resins.

3. The sequencer of claim 1 wherein said hydrophobic resin is C-4 to C-18 alkyl substituted silica or a polymeric hydrophobic resin and said hydrophilic resin is controlled-pore glass or unsubstituted silica.

4. The sequencer of claim 1 wherein said first resin is a first substantially homogeneous mixture and said second resin is a second substantially homogeneous mixture, said first mixture and said second mixture being characterized by respective and opposing electrostatic charges.

5. The sequencer of claim 4 wherein said second mixture includes an electronegatively charged resin and said first mixture includes an electropositively charged resin.

6. The sequencer of claim 5 wherein said electropositively charged resin is a quaternary or tertiary amino substituted macroporous polyolefin or a sulfonate substituted macroporous polyolefin.

7. The sequencer of claim 1 wherein said first and second ports are at substantially opposite locations in said chamber.

8. The sequencer of claim 7 wherein said first resin is adjacent to said first port and said second resin is adjacent to said second port.

9. The sequencer of claim 8 further comprising liquid introduction means for introducing first and second liquids into said first and second ports respectively.

10. The sequencer of claim 9 wherein said chamber has means for reversibly and sealably engaging said liquid introduction means.

11. The sequencer of claim 9 further comprising first and second peptide sequencing reagents and first and second reservoirs containing said first and second peptide sequencing reagents, respectively, said liquid introduction means being in communication with said reservoirs.

12. The sequencer of claim 11 wherein said liquid introduction means comprises first introduction means for introducing said first peptide sequencing reagent into said first port and second introduction means for introducing said second peptide sequencing reagent into said second port.

13. The sequencer of claim 12 wherein said positive pressure means includes pressurizing means for conveying by pressurized gas said first and second reagents to said first and second ports, respectively.

14. The sequencer of claim 12 wherein said first peptide sequencing reagent includes a solution of phenylisothiocyanate or a derivative thereof for coupling with a peptide to be sequenced.

15. The sequencer of claim 14 wherein said solution further includes a polar solvent.

16. The sequencer of claim 15 wherein said solvent is an alkaline buffered aqueous solution.

17. The sequencer of claim 12 wherein said second peptide sequencing reagent includes a substantially nonpolar organic solvent.

18. The sequencer of claim 8 wherein said chamber is an elongated cylinder having first and second ends, said first port having an opening through said first end and said second port having an opening through said second end.

19. The sequencer of claim 1 wherein said first and second chromatography resins are substantially continuous mixtures of chromatography resins.

20. The sequencer of claim 1 further comprising thermal control means for adjusting the temperature of said chamber in coordination with reactions occurring therein.

21. The sequencer of claim 20 wherein said thermal control means is such that it can maintain the temperature of said chamber at about 55° C. for coupling of phenylisothiocyanate to a polypeptide to be sequenced and at about 0° C. to 50° C. for acid extraction.

22. The sequencer of claim 1 further comprising detection means for detecting derivatized amino acid, said detection means being in fluid communication with one of said first and second ports.

* * * * *